United States Patent [19]

Updyke et al.

[11] Patent Number: 6,057,106
[45] Date of Patent: May 2, 2000

[54] SAMPLE BUFFER AND METHODS FOR HIGH RESOLUTION GEL ELECTROPHORESIS OF DENATURED NUCLEIC ACIDS

[75] Inventors: Timothy V. Updyke, Temecula; Roumen A. Bogoev, Escondido; Song-Hua Ke, San Diego, all of Calif.

[73] Assignee: Novex, San Diego, Calif.

[21] Appl. No.: 09/012,257

[22] Filed: Jan. 23, 1998

[51] Int. Cl.[7] .............................. C12Q 1/68; C07H 21/02; C07H 21/04; C12N 15/00
[52] U.S. Cl. ............................ 435/6; 536/23.1; 536/24.3; 935/76; 935/77; 935/78
[58] Field of Search ................................. 435/6; 536/23.1, 536/24.3; 935/76, 77, 78

[56] References Cited

U.S. PATENT DOCUMENTS

| | | | |
|---|---|---|---|
| 4,795,699 | 1/1989 | Tabor et al. | 435/5 |
| 4,936,963 | 6/1990 | Mandecki et al. | 204/182.8 |
| 5,102,784 | 4/1992 | George | 435/6 |
| 5,171,534 | 12/1992 | Smith et al. | 422/82.05 |
| 5,190,856 | 3/1993 | Borresen | 435/6 |
| 5,290,418 | 3/1994 | Menchen et al. | 204/299 |
| 5,370,731 | 12/1994 | Yamashita et al. | 106/22 |
| 5,370,777 | 12/1994 | Guttman et al. | 204/182.8 |
| 5,616,227 | 4/1997 | McCormick | 204/457 |

FOREIGN PATENT DOCUMENTS

WO9506668  3/1995  WIPO.

OTHER PUBLICATIONS

Joseph Sambrook et al., *Molecular Cloning: A Laboratory Manual*, pp. 13.45–13.46 (2d ed. 1989).
"Migration Tables" and "Buffer Selection Guide", NOVEX Brochure, (1991).
"Electrophoresis, The NOVEX System: The Fast, Easy Way To Your Answer!", NOVEX Brochure (1992).
"Technically Speaking . . . , NOVEX Pre–mixed Buffers, Fast, Easy, Reproducible Electrophoresis Buffers", NOVEX Brochure (1993).
Piero Carninci et al., "A Discontinuous Buffer System Increasing Resolution And Reproducibility In DNA Sequencing On High Voltage Horizontal Ultra–Thin Layer Electrophoresis," *Electrophoresis,* vol. 6, pp. 1836–1845 (1995).
"Electrophoresis," Novex Brochure, pp. 54–57 (1996).
"QuickPoint™ Sequencing Cell Instructions," NOVEX Instruction Manual (copyright 1997).
"QuickPoint™ Gel Instruction Booklet," NOVEX Instruction Manual (copyright 1997).
"T7 Sequenase version 2.0 DNA sequencing kit," Sequenase Brochure (copyright 1997).
U. K. Laemmli, "Cleavage of Structural Proteins During the Assembly of the Head of Bacteriophage T4," Nature, vol. 227, pp 680–85 (1970).
Maniatis et al. *Molecular Cloning: A Laboratory Manual,* pp. 151, 156, 200, 475–476 (1982).
"Nucleic Acid Sequencing", p. 75, A Publication of the United States Biochemical Corporation(Copyright 1993).
Liu et al., " Parameters Affecting the Sensitivities of Dideoxy Fingerprinting and SSCP", PCR Methods and Applications 4: 97–108 (1994).
Maniatis et al., Molecular Cloning: A Laboratory Manual, pp. 160 and 455 (1982).

*Primary Examiner*—W. Gary Jones
*Assistant Examiner*—Ethan Whisenant
*Attorney, Agent, or Firm*—Fish & Neave; James Trosino

[57] ABSTRACT

A sample buffer and method are provided for preparing denatured nucleic acids and applying them to gel electrophoresis systems. The sample buffer and method enhance band flatness and sharpness, resulting in higher resolution and throughput.

16 Claims, No Drawings

SAMPLE BUFFER AND METHODS FOR HIGH RESOLUTION GEL ELECTROPHORESIS OF DENATURED NUCLEIC ACIDS

This invention relates to sample buffers and methods for gel electrophoresis. More particularly this invention relates to sample buffers and methods that improve high resolution electrophoretic separation of denatured nucleic acids.

BACKGROUND OF THE INVENTION

Gel electrophoresis is commonly used to separate by molecular size biological molecules, such as deoxyribonucleic acid ("DNA"), ribonucleic acid ("RNA") and proteins. To perform gel electrophoresis, a polymeric gel, such as polyacrylamide, is formed in a glass tube, or between spaced glass or plastic plates. The tube or plates are then placed in a chamber along with anode and cathode elements at the top and bottom of the gel. Sample wells formed in the top of the gel are first filled with running buffer solutions, and then with molecule samples prepared in a sample buffer that may contain a tracking dye. Electrophoretic running buffer solutions containing conductive ions are added to the chamber to make electrical contact between the gel, the samples in the wells and the anode and cathode elements. A voltage is then applied across the gel, which causes the sample molecules and any tracking dye to migrate toward the bottom of the gel, and separate into bands whose migration distance depends on molecular size.

The macromolecule migration rate through the gel generally depends upon five principle factors: (1) the gel porosity; (2) the applied electric field strength; (3) the electrophoresis temperature; (4) the macromolecule charge density; and (5) the macromolecule size and shape. For reproducible high resolution electrophoresis, these five factors generally must be precisely controlled from gel-to-gel and from sample-to-sample.

The first four factors generally do not pose a significant problem for separating nucleic acids. Manufactured precast electrophoresis gels may be used to maintain highly uniform gel-to-gel porosity, and numerous gel types are available for separating different macromolecules. In addition, modern electrophoresis equipment accurately controls temperature and voltage during separation. Further, DNA and RNA charge densities are very uniform because of the repeating structure of the anionic phosphate backbone. This charge uniformity leads to a precise inverse correlation of mobility with molecular length or base number, allowing nucleic acids varying by one base unit to be resolved by electrophoresis.

DNA base sequencing is one of the most useful embodiments of denaturing gel electrophoresis separations. In DNA base sequencing, the DNA sequencing product is denatured and the resulting single stranded DNA sample is applied to the electrophoresis gel. The native structural forms of DNA and RNA result from hydrogen-bonded interactions between complementary sequences of two strands of nucleic acid or between complementary regions in a single strand. These interactions must be completely disrupted prior to and during electrophoresis to eliminate secondary structure so that precise correlation of size with mobility is maintained.

Heat and organic solvents such as formamide and/or urea can be used in aqueous solutions to disrupt hydrogen bonds, resulting in denatured DNA and RNA. Thus, denatured DNA separations typically are performed in 6% polyacrylamide gels containing tris (hydroxy methyl) amino-methane, borate, ethylene diamine tetra-acetic acid ("TBE") gel and running buffer, pH 8.3 to 9.0, with 6 to 8 M urea and/or 2 to 12 M formamide acting as denaturants. In addition, DNA separations typically are performed at high operating temperature, typically 45 to 55° C., to maintain fully denatured DNA.

DNA separations frequently are performed in gels 25 to 50 cm in length and about 0.4 mm thick, cast between two glass sheets. The gel is positioned vertically, and sample molecules, mixed after the sequencing reactions with a sample buffer concentrate, are applied into small sample wells near the top of the gel. These sample wells can be pre-formed in the gel or by use of a "sharks toothed comb," as described by Joseph Sambrook et al., Molecular Cloning: A Laboratory Manual 13.45–13.46 (2d ed. 1989).

The sample application area typically is filled with gel running buffer. The sample molecules, which are more dense than the running buffer, are carefully layered under the running buffer and on top of the exposed gel surface. To achieve sharp, well defined bands, the vertical depth of the sample should be minimized. Because DNA migrates faster in free solution in the loading buffer than it does in the gel, the DNA is concentrated and therefore sharpened at the gel surface before it penetrates into the gel. Nevertheless, dispersion and/or diffusion of the sample upward in the sample well will reduce the efficiency of this sharpening effect and limit the number of bases that can be clearly resolved on a given gel.

To increase resolution, electrophoresis may be performed using gels thinner than 0.4 mm, which create less band dispersion during electrophoretic migration. Recently, Novel Experimental Technology, Inc. ("NOVEX") developed the QuickPoint™ precast minigel (10 cm wide by 12.5 cm long and 0.25 mm thick) for DNA base sequencing. QuickPoint™ is prepared with 6% polyacrylamide, 7M urea and a neutral pH buffer that provides stable electrophoresis and storage conditions. QuickPoint™ gels have very high resolution capabilities, and can be operated with voltage gradients greater than 100 volts/cm, which allows from 60 to over 100 DNA bases to be resolved in less than 10 minutes within an 11 cm gel.

To realize the potential separation efficiency of such thin gels, the sample bands must be very sharp from the beginning of the electrophoresis run. Because the gel is very thin, however, it is more difficult to carefully layer the sample molecules on the gel and minimize dispersion during loading. Also, the sample molecules must be loaded quickly, because the first few samples begin diffusing into the buffer and the gel before the final samples have been loaded and before electrophoresis commences. It is therefore an object of the present invention to provide a method for applying denatured nucleic acid samples to the sample wells in a denaturing electrophoretic gel to maximize sample resolution and throughput.

Once electrophoresis begins and the molecules separate into bands, the bands may widen and begin to curve upward, further impairing fine resolution separation. Band sharpness and flatness are affected by, among other things, re-naturation and diffusion. In addition, any free ions in the sample increase the conductance of the sample region, causing a low voltage drop across the sample region, which increases separation times and further impairs flatness and sharpness.

Prior art electrophoresis systems use sample buffers to increase sample density and enhance band sharpness and flatness. High density samples quickly settle into the sample wells and speed sample loading, and consequently improve resolution. Ideally, an electrophoresis sample buffer provides several important functions:

1. Controls sample zone pH during electrophoresis;
2. Controls ion and sample molecule movement during electrophoresis;
3. Increases sample density and/or viscosity to aid sample loading into the sample wells;
4. Provides tracking dye(s) to aid monitoring the progress of electrophoresis;
5. Provides denaturing agent(s) to disrupt macromolecules to their primary structure; and
6. Provides various chemical reducing and/or chelating agents to control sample chemistries.

Prior art sample buffers that provide all six functions are commonly used in discontinuous, reducing, sodium dodecyl sulfate polyacrylamide gel electrophoresis ("SDS-PAGE") developed by U. K. Laemmli, 227 Nature 680–86 (1970), and by NOVEX, NOVEX Catalogue 59–73 (1996). In particular, these prior art sample buffers concentrate the sample molecules into very sharp starting zones. This process, called "stacking," is controlled by the common buffering ion contained in the buffer system comprised of the gel, sample buffer and running buffers. The common buffering ion typically is an amine or substituted amine, such as tris (hydroxy methyl) amino-methane ("Tris") or bis-(2-hydroxyethyl) iminotris (hydroxymethyl) methane ("Bis-Tris"), respectively, with a $pK_a$ close to the desired pH of the buffer system for maximum pH control.

Stacking occurs when the anions used to titrate the Tris or Bis-Tris to the desired pH of the buffer system move faster than the sample molecules, and the anions in the running buffer are slower than the sample molecules. Under this condition, the sample molecules become concentrated, or stacked, and the extent of the stacking effect is proportional to the concentration of the leading anions in the gel and/or sample buffer. Stacking enhances the subsequent sharpness of the separations, and is critical to high resolution electrophoresis.

Prior art sample buffers for denaturing nucleic-acid electrophoresis, however, have not been designed to utilize this stacking effect. The primary reason is that the buffer systems used for nucleic acid electrophoresis generally are continuous, having the same buffering amines and titrating anions in the gel, running buffer and, occasionally, the sample buffer. For example, NOVEX's TBE-Urea sample buffer contains (1) TBE buffer; (2) urea, which acts as a denaturant; (3) ethylene diamine tetra-acetic acid ("EDTA"), which acts as chelating agent to bind divalent cations in the sample; and (4) Ficoll™ (type 400), a highly branched polysaccharide of 400 kDa that increases the sample density and viscosity and retards molecular diffusion.

Further, prior art sample buffers for denaturing nucleic acid polyacrylamide gel electrophoresis have been developed to enhance ion chelation, but not necessarily to improve stacking. For example, the Sequenase™ Version 2.0 DNA Sequencing Kit (United States Biochemical/Amersham Life Science) uses the most common prior art sample buffer (or stop solution) and method for denaturing DNA. These buffers contain (1) 95% formamide; (2) 20 mM EDTA, titrated with sodium hydroxide to pH 8.0; and (3) 0.05% bromophenol blue and 0.05% xylene cyanol FF. Formamide acts as a denaturant, and EDTA acts as an ion-chelating agent to bind magnesium ions, as required for sequencing enzyme activity and native DNA structure.

The Sequenase™ method for denaturing DNA samples combines 3.5 volumes of sample molecules with 4 volumes of the sample buffer/stop solution, resulting in 10.7 mM EDTA and 51% formamide in the sample wells. A common modification of the Sequenase™ method combines 6 volumes of sample molecules with 4 volumes of sample buffer/stop solution, resulting in 8 mM EDTA and 38% formamide in the sample wells.

In addition, Tabor et al. U.S. Pat. No. 4,795,699 ("Tabor") describes a DNA sequencing analysis in which a sample buffer containing 90% (volume/volume) formamide, 10 mM EDTA, and 0.10% (weight/volume) xylene cyanol is added to each sequencing reaction sample before gel electrophoresis. To prepare denatured DNA samples for sequencing analysis, Tabor's method combines 3 volumes of DNA sequencing reaction samples with 6 volumes of sample buffer, resulting in a 6.6 mM concentration of EDTA and 60% concentration of formamide in the sample wells of the sequencing gels.

Although the NOVEX TBE-urea sample buffer provides all but the stacking functions, and works reasonably well for standard denatured nucleic acid analyses, it does not provide maximum denaturing capacity when used in DNA sequencing. Additionally, TBE buffer has a relatively high pH (8.3) that hydrolyzes the urea amide groups, thereby creating highly conductive ions, changes in pH and reductions in denaturing strength that cause non-uniform results. Further, because all prior art sample buffers have pH ranges from 8 to 9, hydrolysis of urea and formamide is a problem for all prior art sample buffers.

Moreover, prior art sample buffers containing EDTA are titrated by adding sodium hydroxide. However, sodium hydroxide produces free sodium ions, which increases sample conductance, slows separation, increases heat generation, and enhances convective mixing and diffusion of sample molecules. It therefore also would be desirable to produce a neutral pH sample buffer that contains high EDTA concentration, but that has low sample conductance.

Further, the Sequenase™ and Tabor sample buffers enhance ion chelation, but do not sufficiently increase sample solution density. In addition, both buffers increase conductivity and therefore increase separation time. It therefore would be desirable to provide a sample buffer that enhances ion chelation, increases sample solution density, and decreases sample solution conductivity.

Additionally, although prior art sample buffers achieve some stacking and ion chelation, such systems have not been optimized for this purpose. It therefore also would be desirable to produce a sample buffer that enhances electrophoresis resolution by completely denaturing the sample molecule, enhancing ion chelation and stacking, and inhibiting diffusion.

SUMMARY OF THE INVENTION

It is an object of this invention to provide a method for applying denatured nucleic acid samples to the sample wells in a denaturing electrophoresis gel to maximize sample resolution and throughput.

It is another object of this invention to provide a neutral pH sample buffer that contains high EDTA concentration, but that has low sample conductance.

It is an additional object of this invention to provide a sample buffer that enhances ion chelation, increases sample solution density, and decreases sample solution conductivity.

It is a further object of this invention to produce a sample buffer that enhances electrophoresis resolution by completely denaturing the sample molecules, enhancing ion chelation and stacking, and inhibiting diffusion.

In accordance with this invention, applicants describe a sample buffer and method that maximizes denaturation, enhances ion chelation and stacking, and reduces diffusion. In addition, applicants describe a gel electrophoresis method that maximizes sample resolution and throughput.

The above and other objects and advantages of the present invention will be apparent upon consideration of the following detailed description.

DETAILED DESCRIPTION OF THE INVENTION

Applicants describe a sample buffer and method that facilitates high resolution electrophoretic separation. Samples prepared using these sample buffers and methods exhibit enhanced band sharpness and flatness.

Sample buffers in accordance with this invention contain (1) urea, (2) formamide and (3) a polysaccharide. The formamide and urea denatures the DNA sample and inactivates enzymatic activity in the reaction mixtures. In addition, formamide and urea increase sample density, which causes the molecules in the samples to quickly sink in the sample wells and therefore enhance stacking.

As used herein, polysaccharide means two or more saccharides, and includes, but is not limited to disaccharides, linear polysaccharides and branched polysaccharides. Preferred embodiments of the sample buffer of the present invention include Ficoll™, a branched polysaccharide that increases density and slightly increases viscosity, and minimizes DNA and RNA diffusion into the walls of the sample well. Ficoll™ also decreases the rate of complimentary DNA and RNA re-annealing, thereby producing homogeneous structural forms and improving band sharpness and flatness. Persons of skill in the art would understand that other polysaccharides that would be useful in the buffer of the present invention include, but are not limited to, disaccharides such as sucrose and linear polysaccharides such as dextran.

Alternative embodiments of sample buffers of the present invention further include a primary or substituted organic amine and an acid such as a zwitterionic, inorganic or organic acid. Preferred sample buffers of the present invention include primary or substituted organic amines with a $pK_a$ of about 6.5 to 9.0, titrated with a divalent cation chelating agent. Preferably the primary or substituted organic amine is Tris or Bis-Tris. Persons of skill in the art would recognize that other primary or substituted organic amines that would be useful in the buffer of the present invention include, but are not limited to, to N-(2-hydroxyethyl) morpholine, diethanolamine and triethanolamine.

Preferably, the acid is the divalent cation chelating agent EDTA. EDTA serves both as an ion-chelating agent to remove magnesium ions, which are required for Sequenase™ and other polymerases, and as a leading ion during gel electrophoresis to provide the initial-transient stacking effect of DNA and RNA bands. Persons of skill in the art would realize that other acids would be useful in the buffer of the present invention. Such acids include, but are not limited to: (1) organic acids such as formic acid, acetic acid and propionic acid; (2) inorganic acids such as hydrochloric acid, phosphoric acid and sulfuric acid; and (3) zwitterionic acids such as (2-(N-morpholino) ethanesulfonic acid) ("MES"), aspartic acid and glutamic acid.

Further alternative embodiments of the sample buffer of the present invention also include one or more tracking dyes. Tracking dyes may be used to monitor the progress of electrophoresis and to indicate the positions of nucleic acids of a particular base-length. For instance, in the NOVEX 6% QuickPoint™ gels, the bromophenol blue dye band migrates with 26 base-lengths of denatured DNA. Likewise, the acid red 4 dye co-migrates with 60 base-lengths and the xylene cyanol FF co-migrates with 110 base-lengths of denatured DNA. For some applications, however, such as automated DNA sequencing, tracking dyes should not be used because the dyes interfere with photometric detection of electrophoretically separated DNA molecules tagged with fluorescent dye molecules.

In embodiments of the sample buffer of the present invention, a sample buffer solution comprising a primary organic amine or substituted amine with a $pK_a$ of about 6.5 to 9.0, preferably between about 6.5 to 7.0, is titrated with EDTA, so that the pH of the sample buffer is between about pH 6.5 and pH 9.0, preferably between about pH 6.5 to pH 7.5, and most preferably pH 6.5 to pH 7.0.

The urea concentration may be about 6M (36% weight/volume) to about 8M (48% weight/volume), preferably 7M (42% weight/volume). The formamide concentration may be about 30% to about 45% (volume/volume), preferably about 40%. Branched polysaccharides of about 300 kDa to about 500 kDa, at a concentration of about 6% to about 18%, and most preferably branched polysucrose of about 300 kDa to about 500 kDa (Ficoll™, type 400), are dense (approximately 1.4 to 1.6 g/mL) and highly soluble in water and polar organic solvents, such as formamide and may increase viscosity.

Preferred embodiments of the sample buffer of the present invention contain 7M urea, 20–45% (volume/volume) formamide, 6–18% (weight/volume) Ficoll™ (type 400), 21–50 mM EDTA (free acid), 100 mM–200 mM Bis-Tris, and tracking dyes including 0.025% (weight/volume) xylene cyanol FF, 0.025% (weight/volume) bromophenol blue and 0.025% (weight/volume) acid red 4. Persons of skill in the art will recognize that all three dyes need not be used together and that other tracking dyes may be useful in the sample buffer.

The most preferred embodiment of the sample buffer of the present invention contains 7M urea, 40% (volume/volume) formamide, 12% (weight/volume) Ficoll™ (type 400), 30 mM EDTA (free acid), 100 mM Bis-Tris, and tracking dyes including 0.025% (weight/volume) xylene cyanol FF, 0.025% (weight/volume) acid red 4 and 0.025% (weight/volume) bromophenol blue, to form a solution having a density of 1.18 g/ml (20° C.) and a pH of 7.0.

In preferred methods for applying denatured nucleic acid samples to the sample wells in a denaturing electrophoretic gel, a sample solution first is prepared by combining 3 volumes of nucleic acid samples with 7 volumes of sample buffers of the present invention. Next, the sample solution is heated at 75° C. for 2 minutes and placed in an ice water bath for 2 minutes. Finally, about 0.2 µL to about 3 µL is pipetted into the top portion of each sample well. For gel thicknesses of about 0.25 mm, about 0.4 µl sample solution is pipetted into the top portion of each sample well.

In particularly preferred methods, a sample solution first is prepared by combining 3 volumes of nucleic acid samples with 7 volumes of the most preferred sample buffer described above. The resulting sample solution contains 21 mM EDTA, 4.9 M urea, 28% formamide, 8.4% Ficoll™, and has a density of 1.13 g/ml (the same as pure formamide at 20° C.) and a relative viscosity of about 5 cP (20° C.). The sample solution is heated and then cooled as described above, and then about 0.2 µL to about 3 µL is pipetted into the top portion of each sample well. For gel thicknesses of about 0.25 mm, about 0.4 µL sample solution is pipetted into the top portion of each sample well. The described methods are very fast and easy and result in sharp bands, long sequencing read-lengths of all loaded samples, and consequently high sample throughput.

These and other embodiments can be understood by reference to the following illustrative and comparative examples.

EXAMPLES

Bis-Tris was purchased from Research Organics (Cleveland, Ohio). EDTA, formamide, Ficoll™ (type 400) and bromophenol blue were purchased from Sigma (St. Louis, Mo.). Urea was purchased from Amresco (Solon, Ohio). Acid red 4 was purchased from Aldrich Chemical Co. (Milwaukee, Wis.). Xylene cyanol FF was purchased from Serva (Heidelberg, Germany). All other chemicals were reagent, "ultra pure" or "electrophoresis grade" from standard sources. DNA Sequencing gels, QuickPoint™, and running buffer were from NOVEX (San Diego, Calif.). The gels were 6% polyacrylamide and contained 7M urea in a neutral pH buffer. The gels are manufactured a minigel format with dimensions 10 cm wide by 12.5 cm long with 0.25 mm spacers. Pipette tips (10 µL, flat and round designs) were purchased from Rainin (Woburn, Mass.).

DNA sequencing samples were prepared using a Sequenase™ Version 2.0 DNA Sequencing Kit from Amersham Life Science (Cleveland, Ohio). M13mp18 single stranded DNA was used in the reaction as a template. The sequencing samples were labeled with dATP, αS, $^{35}$S purchased from New England Nuclear (Boston, Mass.). BioMax MR film purchased from Kodak (Rochester, N.Y.) was used for autoradiographic visualization of the labeled DNA bands. The sequencing reactions were stopped by adding either the Sequenase™ stop solution/sample buffer from the kit or various examples of our sample buffer invention. All samples were heated at 75° C. for 2 minutes and chilled at 0° C. in a ice water bath for 2 minutes before applying the samples to the wells of the sequencing gels by standard "underlay" pipetting methods or the method according to our invention.

Electrophoresis was performed at 50° C. in QuickPoint™ Rapid DNA Sequencing Cell at 1200 V constant voltage according to the manufacturer's instructions and electrophoresis was stopped when the bromophenol blue dye reached the bottom of the gel (about 9 minutes). The gels were fixed and dried according to the manufacturer's instructions, and the DNA bands were visualized after exposing the film overnight.

Example 1

The preferred embodiment sample buffer for minigel DNA sequencing was prepared except that various concentrations of EDTA free acid (20, 30, 40, 50, 60, 80, 100 mM) were added to a constant amount of Bis-Tris free base (100 mM). The resulting sample buffer pH range was from 7.2 at 20 mM EDTA to 6.5 at 50 mM; at 60 mM and higher concentrations of EDTA some portion of the EDTA remained insoluble and these sample buffers were not further tested. The remaining composition of the sample buffers was 7M (42%, weight/volume) urea, 40% (volume/volume) formamide, 12% (weight/volume) Ficoll (type 400), 0.025% (weight/volume) bromophenol blue, 0.025% (weight/volume) acid red 4, 0.025% (weight/volume) xylene cyanol FF. Four sets of DNA sequencing reactions were stopped by adding 7 volumes (14 µL) of the test sample buffers to 3 volumes (6 µL) of the reaction samples. In this example, the EDTA concentrations in final samples were 14 mM, 21 mM, 28 mM and 35 mM. The samples were heated, chilled and applied to the top portion of the sample wells of the sequencing gels. Standard electrophoresis, processing and autoradiography were performed as above. The results showed that with 14 mM EDTA in the sample wells, the DNA base sequence could be read from 70 to 83 bases. With 21 mM to 35 mM EDTA, the bands were slightly sharper and the DNA sequences could be read from 83 to 85 bases. Therefore, the higher EDTA concentrations significantly improve the reading length of the sequencing gel.

Example 2

Applicants prepared two sets of DNA sequencing reactions. The first set was stopped by adding 7 volumes (14 µL) stop solution from the Sequenase™ kit to 3 volumes (6 µL) of the sequencing reactions. The second set was stopped by adding 7 volumes (14 µL) of the preferred embodiment of the sample buffer to 3 volumes (6 µL) of the sequencing reactions. The samples were heated and then chilled by the standard method. The samples were applied as follows:

1. Samples prepared with the Sequenase™ stop solution were applied to two minigels using a prior art method: by inserting 170 µm, flat pipette tips inside the wells and dispensing the samples on the bottom of the wells.

2. Samples prepared with the Sequenase™ stop solution were applied to two minigels using the preferred method of this invention: by touching the pipette tip on the top of the well and dispensing the sample without inserting the tip inside the well.

3. Samples prepared with the preferred sample buffer were applied to two minigels using the preferred method of this invention.

The prior art loading method proved to be very difficult, taking more than 13 minutes to load both gels (8 sets of 4 samples). In particular, air bubbles from the pipette frequently became trapped in the sample wells and were difficult to remove. In addition, the samples dispersed and mixed with the buffer in the sample well, and an uneven sample quantity was dispensed when mixing occurred. As a result of these problems, the sequencing results were very inconsistent: between 0 and 76 bases were readable. Further, the bands were U-shaped, and some samples were unreadable as a result of DNA band fuzziness.

By contrast, the preferred method of this invention for applying the samples was fast and simple, requiring only 5.5 minutes to load both gels. Significantly, however, the samples prepared with the Sequenase™ stop solution produced fuzzy bands, which resulted in read lengths of approximately 62 bases. Two samples applied to the final wells had sufficient sharpness to read 76 bases.

Samples prepared and loaded using the sample buffer and method of the present invention produced the sharpest and flattest bands. Indeed, the results showed consistently good quality across both gels (all 8 sets of samples), which resulted in read lengths of 83 bases.

These results, and those of Example 1, demonstrate that the sample buffer of the present invention significantly improves the sharpness and flatness of the DNA bands compared to the most common prior art sample buffer, even when it is used in more concentrated amounts than the standard method. The results additionally show that even when we use a sample buffer containing 20 mM EDTA, which is the same concentration as the Sequenase™ buffer solution, the density increase caused by the polysaccharide improves performance.

The sample buffer and method of the present invention results in sample densities of about 1.13 g/mL, whereas samples prepared with the Sequenase™ stop solution and applied using the invented method have densities of about 1.09 g/mL. In addition, the presence of Ficoll™ in the samples provides a slight viscosity increase which decrease the dispersion and diffusion of the DNA molecules in the samples. By using the sample buffer and method of the present invention, DNA read lengths and sample throughput are increased.

Although the invention has been explained in relation to its preferred embodiments, it will be understood that various modifications thereof will become apparent to those skilled in the art. The foregoing disclosure is not intended to be construed to limit the present invention, or to otherwise exclude any such other embodiments, adaptions, variations and equivalent arrangements, the present invention being limited only by the claims appended hereto and the equivalents thereof.

We claim:

1. A sample buffer for gel electrophoresis of denatured nucleic acid, the sample buffer comprising urea, formamide, a polysaccharide, and a component that results in stacking in a sample well of an electrophoretic gel, the stacking component comprising a primary or substituted organic amine, and an acid selected from the group consisting of zwitterionic, inorganic and organic acids.

2. The sample buffer of claim 1 comprising about 7 M urea, from about 30% to about 45% (volume/volume) formamide, and from about 6% to about 18% (weight/volume) polysaccharide.

3. The sample buffer of claim 1, wherein the polysaccharide is selected from the group consisting of disaccharides, linear polysaccharides and branched polysaccharides.

4. The sample buffer of claim 1 further comprising at least one tracking dye selected from the group consisting of xylene cyanol FF, acid red 4 and bromophenol blue.

5. The sample buffer of claim 1, wherein the primary or substituted organic amine has a $pK_a$ of about 6.5 to about 9.0.

6. The sample buffer of claim 1, wherein the sample buffer has a pH of about 6.5 to about 9.0.

7. The sample buffer of claim 1, wherein the organic acid is a divalent cation chelating agent.

8. The sample buffer of claim 7, wherein the divalent cation chelating agent is ethylene diamine tetra-acetic acid.

9. The sample buffer of claim 8 comprising from about 21 mM to about 50 mM ethylene diamine tetra-acetic acid.

10. The sample buffer of claim 1, wherein the primary or substituted organic amine is selected from the group consisting of bis-(2-hydroxyethyl) iminotris (hydroxymethyl) methane and tris (hydroxy methyl) amino-methane.

11. The sample buffer of claim 1, wherein the sample buffer has a pH of about 7.0.

12. A method for applying denatured nucleic acid samples to a plurality of sample wells in a denaturing electrophoretic gel, the method comprising:

preparing a sample solution by dissolving the nucleic acid samples in a sample buffer comprising urea, formamide and a polysaccharide; and pipetting the sample solution into an upper portion of the sample wells.

13. The method of claim 12, wherein:

the sample buffer further comprises ethylene diamine tetra-acetic acid; and preparing the sample solution comprises dissolving the nucleic acid samples in the sample buffer to obtain a concentration from about 15 to about 35 mM ethylene diamine tetra-acetic acid.

14. The method of claim 12, wherein:

the denaturing electrophoretic gel has a thickness of about 0.4 mm or less; and the step of pipetting the sample solution into the upper portion of the sample wells comprises pipetting about 0.2 μL to about 3 μL of sample solution into the upper portion of each sample well.

15. The method of claim 12, wherein:

the denaturing electrophoretic gel has a thickness of about 0.25 mm; and the step of pipetting the sample solution into the upper portion of the sample wells comprises pipetting about 0.4 μL of sample solution into the upper portion of each sample well.

16. The method of claim 12, wherein preparing the sample solution further comprises:

combining about 3 volumes of the nucleic acid samples with about 7 volumes of the sample buffer;

heating the sample solution for about 2 minutes at about 75° C.; and cooling the sample solution for about 2 minutes in ice water.

* * * * *